(12) United States Patent
Hirata et al.

(10) Patent No.: US 7,300,672 B2
(45) Date of Patent: Nov. 27, 2007

(54) TITANIUM-GROUP METAL CONTAINING HIGH-PERFORMANCE WATER, AND ITS PRODUCING METHOD AND APPARATUS

(75) Inventors: Yoshihiro Hirata, Kyoto (JP); Yoshio Ueda, Kyoto (JP); Hiroaki Takase, Kyoto (JP); Kazuaki Suzuki, Kyoto (JP)

(73) Assignee: Phild Co., Ltd., Kyoto (JP)

( * ) Notice: Subject to any disclaimer, the term of this patent is extended or adjusted under 35 U.S.C. 154(b) by 525 days.

(21) Appl. No.: 10/492,246

(22) PCT Filed: Oct. 10, 2002

(86) PCT No.: PCT/JP02/10524

§ 371 (c)(1),
(2), (4) Date: Jun. 21, 2004

(87) PCT Pub. No.: WO03/033417

PCT Pub. Date: Apr. 24, 2003

(65) Prior Publication Data

US 2004/0237716 A1   Dec. 2, 2004

(30) Foreign Application Priority Data

Oct. 12, 2001   (JP)   .................... 2001-315446

(51) Int. Cl.
- *A61K 33/24* (2006.01)
- *A61K 8/04* (2006.01)
- *A61K 8/28* (2006.01)
- *A61K 8/29* (2006.01)
- *B22F 9/14* (2006.01)
- *B01F 3/12* (2006.01)
- *C02F 1/68* (2006.01)

(52) U.S. Cl. ................ 424/617; 424/489; 204/157.44; 252/182.33; 516/78; 75/346; 75/370

(58) Field of Classification Search ........... 424/617; 204/157.44
See application file for complete search history.

(56) References Cited

U.S. PATENT DOCUMENTS

| 5,587,170 | A | 12/1996 | L'Oreal et al. |
| 5,707,419 | A | 1/1998 | Tsantrizos et al. |
| 6,869,626 | B1 * | 3/2005 | Hirata et al. ............. 426/66 |
| 7,108,735 | B2 * | 9/2006 | Hirata et al. ............. 75/355 |
| 2004/0091552 | A1 * | 5/2004 | Hirata et al. ............. 424/649 |
| 2004/0107798 | A1 * | 6/2004 | Hirata et al. ............. 75/331 |
| 2004/0118244 | A1 * | 6/2004 | Hirata et al. ............. 75/331 |
| 2004/0131566 | A1 * | 7/2004 | Hirata et al. ............. 424/70.1 |
| 2005/0019289 | A1 * | 1/2005 | Hirata et al. ............. 424/70.1 |
| 2005/0092132 | A1 | 5/2005 | Hirata et al. |

FOREIGN PATENT DOCUMENTS

| EP | 1 374 836 A1 | 1/2004 |
| EP | 1 393 841 A1 | 3/2004 |
| JP | 02-166202 | 6/1990 |
| JP | 04-122433 | 4/1992 |
| JP | 06-093311 | 4/1994 |
| JP | 11-228141 | 8/1999 |
| JP | 2001-137866 | 5/2001 |
| JP | 2001-314878 | 11/2001 |
| WO | WO 03/032932 A1 | 4/2003 |

* cited by examiner

*Primary Examiner*—John Pak
(74) *Attorney, Agent, or Firm*—Knobbe, Martens Olson & Bear LLP

(57) ABSTRACT

Produce titanium-group metal micro-dispersion water that contains ion vapor of titanium-group metal in micro-dispersed state and that can be used as a material for health products, medical products, cosmetics, etc., by using an apparatus comprising a water tank, a high-voltage discharge generator equipped with a titanium-group metal electrode and its counter electrode, a water inlet, an outlet for produced water, and a titanium-group metal electrode feeder, in a manner causing plasma discharge in water between the titanium-group metal electrode and its counter electrode.

8 Claims, 2 Drawing Sheets

Production Flow Chart of High-Function Water Containing Titanium-Group Metal

TITANIUM-GROUP METAL CONTAINING HIGH-PERFORMANCE WATER, AND ITS PRODUCING METHOD AND APPARATUS

This application is the U.S. National Phase under 35 U.S.C. §371 of International Application PCT/JP02/10524, filed on Oct. 10, 2002, which claims priority of Japanese Patent Application No. 2001-315446 filed on Oct. 12, 2001. The International Application was published under PCT Article 21(2) in a language other than English.

FIELD OF THE INVENTION

This invention relates to high-function water in which super-fine titanium-group metal particles are micro-dispersed.

The invention also relates to a method for producing high-function water in which super-fine titanium-group metal particles are micro-dispersed, as well as an apparatus for producing the same.

The invention further relates to health products, medical products and cosmetics utilizing the aforementioned high-function water.

DESCRIPTION OF THE RELATED ART

Titanium-group metals including titanium, zirconium and hafnium are relatively new metal materials discovered much more recently than iron, copper, aluminum, etc. Particularly titanium metal, which is a representative metal among the aforementioned titanium-group metals, is lightweight and offers excellent strength at high temperature. Because of these properties, titanium metal is already used in wide industrial applications, such as jet engine material for aircraft and spaceship, tube and tube plate comprising heat-exchangers used for nuclear or thermal power generation, and articles of daily use such as eyeglass frame and golf club head. The applications of titanium metal are expected to grow further.

A large number of examples have been known to date regarding the use of titanium metal in articles of daily use, health/medical products and cosmetics. These examples include barber's scissors with titanium film coatings (Japanese Patent Application Laid-open No. 62-268584), the utilization of far-infrared ray through molten titanium metal (Japanese Patent Application Laid-open Nos. 61-59147, 1-155803 and 3-112849), bedding (Japanese Patent Application Laid-open No. 8-322695), cooking utensil (Japanese Patent Application Laid-open No. 9-140593), eye mask (Japanese Patent Application Laid-open No. 10-71168), health-maintaining equipment (Japanese Patent Application Laid-open Nos. 11-285541 and 11-285543), health band (Registered Japanese Utility Model No. 3045835) and health slippers (Registered Japanese Utility Model No. 3061466).

However, the example of utilizing titanium-containing water as function water is limited to a production apparatus that uses titanium metal in the cathode to produce drinking water through electroosmosis (Japanese Patent Application Laid-open No. 50-40779).

Likewise, very few applications are known that pertain to use of titanium-group metals, other than titanium, in bioactive materials, food materials, medical products, etc.

SUMMARY OF THE INVENTION

Use of titanium-group metals in bioactive materials, food materials, medical products, etc., is generating keen interests. However, logical explanations as to how these metals can be utilized in such applications have not been offered.

The present invention aims to apply the almost infinite utilities of these titanium-group metals in the areas of bioactive materials and health/medical products in particular.

The present invention provides high-function water in which titanium-group metal is micro-dispersed, by converting titanium-group metal into metal ion vapor via plasma discharge in water and causing the vapor to contact water.

In addition, the high-function water offering high bioactivity as obtained by the present invention has been found useful as a material for health products, medical products and cosmetics.

Further, the present invention provides a method and apparatus for efficiently producing the aforementioned high-function water containing titanium-group metal that offers bioactivation effects in health/medical products, etc.

In the context of the present invention, "titanium-group metal micro-dispersion water" refers to water in which super-fine titanium-group metal particles of micron to nano-scale are micro-dispersed.

The basic feature of the present invention lies in the generation of high-function water in which super-fine titanium-group metal particles are micro-dispersed, by way of plasma discharging of titanium-group metal in water to convert it into metal ion vapor. Specifically, the present invention comprising (1) through (4) below:

(1) A method for producing micro-dispersion water of super-fine titanium-group metal particles, wherein titanium-group metal is converted into ion vapor through plasma discharge in water in a manner allowing the vapor to contact, and micro-disperse in, water.

(2) An apparatus for producing micro-dispersion water of super-fine titanium-group metal particles, comprising a water tank, a high-voltage discharge generator equipped with a titanium-group metal electrode and its counter electrode, a water inlet, an outlet and a discharge pump for discharging processed water, an electrode-vibration/sliding device, and a feeder of the titanium-group metal electrode.

(3) High-function water in which super-fine titanium-group metal particles are micro-dispersed.

(4) A health product, medical product or cosmetic product whose main ingredient is the high-function water specified in (3).

In the present invention, a filter system may also be attached as an adjunct to the aforementioned apparatus for producing micro-dispersion water of super-fine titanium-group metal particles, in order to remove fine titanium-group metal particles of larger particle size that are not micro-dispersed.

Generally in a water dispersion or mixed solution in which fine particles of titanium-group metals or oxides of these metals are simply dispersed, the titanium-group metal settles and separates within a short period of time. The titanium-group metal micro-dispersion water obtained by the present invention does not cause the titanium-group metal particles in it to settle.

In other words, the most significant feature of the titanium-group metal micro-dispersion water obtained by the present invention is that the micro-dispersed titanium-group metal generated by plasma discharge in water remains micro-dispersed in a stable manner for a long period of time without settling or otherwise separating from water.

The titanium-group metal micro-dispersion water obtained by the present invention exhibits the surprising, remarkable effect of providing, through an interaction of water molecules and titanium-group metal, high-function water that offers bioactivation functions that can be favorably applied in health products, medical products, cosmetics, etc.

The high-function titanium-group metal micro-dispersion water obtained by the present invention can be used in health products such as motor-function enhancing creams, medical products such as antibacterial agents, and cosmetics such as UV-protection products.

The titanium-group metal micro-dispersion water obtained by the present invention can be used suitably for the above purposes today, but it is believed that this micro-dispersion water will provide an innovative bioactive material that would fully answer the needs of today's health-conscious consumers. The mechanism as to why a micro-dispersion water of titanium-group metal provides excellent bioactive efficacies is not yet clear. The inventors are working diligently to find scientific explanations for these efficacies.

DESCRIPTION OF THE SYMBOLS

Figure 1:
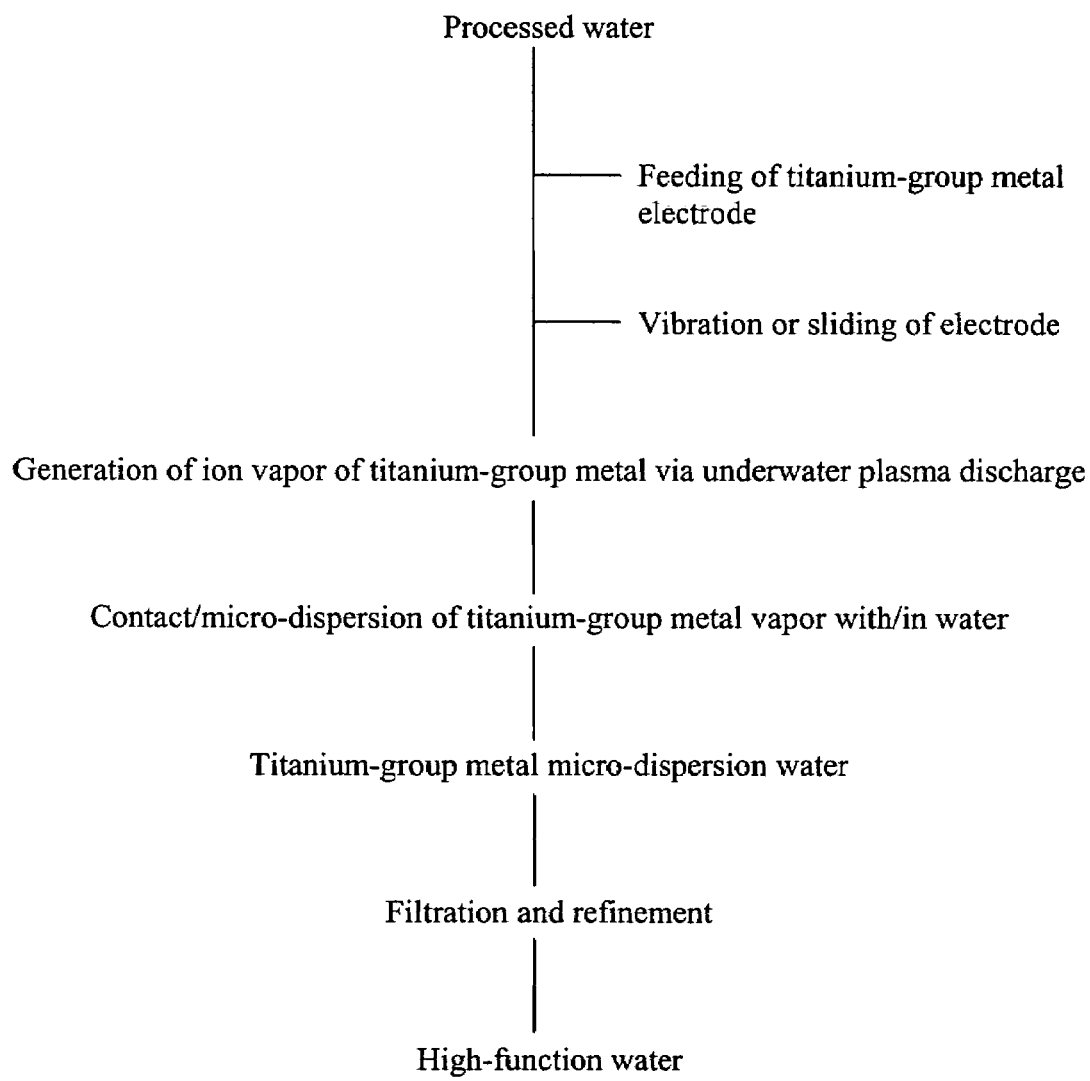
FIG. 1: Production flow chart of titanium-group metal micro-dispersion water as proposed by the present invention

1: High-voltage discharge generator
2: Power supply for high-voltage/current discharge
3: Water tank
4: Titanium-group metal electrode feeder
5: Electrode-vibrating/sliding device
6: Titanium-group metal electrode
7: Counter electrode
8: Water inlet to water tank
9: Outlet for titanium-group metal micro-dispersion water
10: Discharge pump
11: Filter system
12: High-function water

BEST MODE FOR CARRYING OUT THE INVENTION

The titanium-group metal micro-dispersion water obtained by the present invention is a new product not heretofore available.

The present invention also provides a new method and apparatus for producing water that contains metal ion vapor, wherein the production of such water is based on melting titanium-group metal not through general methods like thermal melting that are commonly used to melt metal, but by causing plasma discharge in water.

Specifically, after studying ways to efficiently and economically produce titanium-group metal micro-dispersion water, as well as ways to apply such water to bioactivation purposes, the inventors conceptualized a method to cause plasma discharge in water between a titanium-group metal electrode and its counter electrode, thereby allowing the generated titanium-group metal ion vapor to contact and micro-disperse in water, wherein the method also incorporates a measure to prevent production of substances other than water and titanium-group metal.

The method proposed by the present invention does not require the production conditions to be controlled in order to efficiently add excellent bioactivity to the obtained water. Under the aforementioned production method, an appropriate filter system is necessary because not only micro-dispersed titanium-group metal but also a trace amount of fine metal-oxide particles of larger size than the target super-fine particles will be produced in water.

A method for producing stable micro-dispersion water in which titanium-group metal is micro-dispersed as obtained through the aforementioned method under the present invention, as well as an apparatus to embody this method, are explained according to the drawings.

Figure 2:
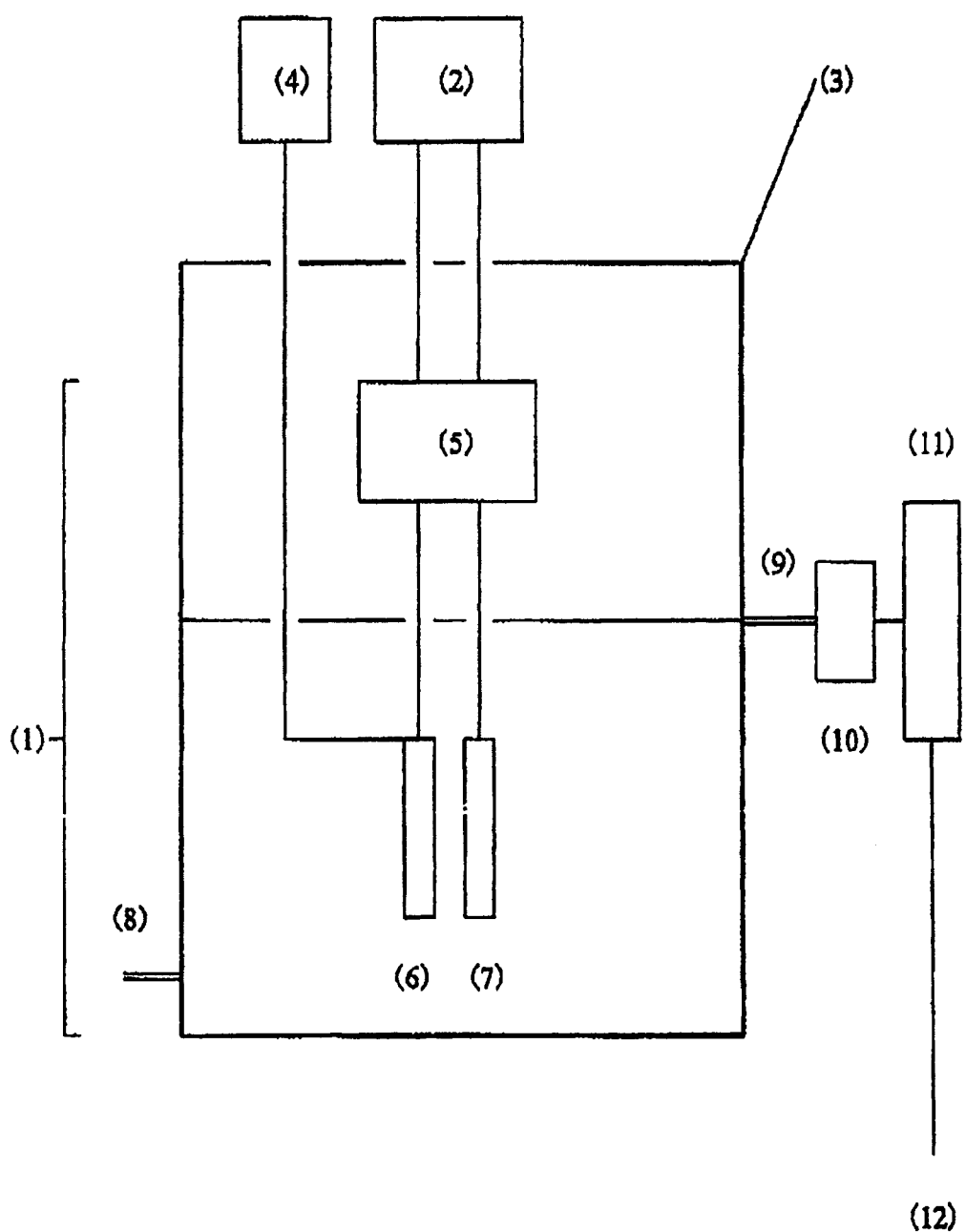
FIG. 2: Schematic drawing of an apparatus for producing titanium-group metal micro-dispersion water as proposed by the present invention

FIG. 1 is a production flow chart of titanium-group metal micro-dispersion water as proposed by the present invention, while FIG. 2 illustrates an apparatus for producing titanium-group metal micro-dispersion water as proposed by the present invention.

The apparatus for producing titanium-group metal micro-dispersion water as proposed by the present invention, as shown in FIG. 2, comprising a high-voltage discharge generator (1) installed in a water tank (3) used for producing water in which titanium-group metal is micro-dispersed, an electrode made of titanium-group metal (6), and a filter system (11) to filter titanium-group metal micro-dispersion water.

The basic structure of the water tank (3) proposed by the present invention comprises an apparatus for producing micro-dispersion water in which titanium-group metal is micro-dispersed (12), comprising the high-voltage discharge generator (1) equipped with the titanium-group metal electrode (6) and its counter electrode (7), a water inlet (8), an outlet (9) through which to discharge titanium-group metal micro-dispersion water, a discharge pump (10), an electrode-vibrating/sliding device (5), and a feeder of titanium-group metal electrode (4). The filter system (11) to filter the produced titanium-group metal micro-dispersion water is also attached as an adjunct.

The water tank proposed by the present invention is made of metal, or preferably steel, and a pressure-resistant container that can withstand the pressures generated during underwater plasma discharge is sufficient. The water tank (3) contains the high-voltage discharge generator (1) equipped with the titanium-group metal electrode (6) and its counter electrode (7), and the titanium-group metal electrode (6) is successively fed into the tank through the feeder (4) in accordance with the rate of micro-dispersion. When current is supplied between the electrodes, plasma discharge occurs in water and metal ion vapor is released, which then contacts, and micro-disperses, in water. Micro-dispersion water containing this micro-dispersed metal is taken out of the outlet (9) in the water tank and sequentially filtered through the filter system (11) provided as appropriate.

Because the titanium-group metal is micro-dispersed in water in vapor state, the metal that has very strong hydrophilic property remains micro-dispersed in water in a stable manner and will not settle even when a coagulating agent is added.

At this time, vibrating or sliding the titanium-group metal electrode of the high-voltage discharge generator in the water tank will prevent the electrode from fusing, thereby making it easy to control the amount of micro-dispersed molecules for generation of instant arc. Additionally, there is no need to change the power supply for each different application, since the amount of current flowing through the circuit can be easily changed by adjusting the diameter and length of the counter electrode made of carbon, etc.

As explained above, the present invention provides a method and apparatus for producing newly developed micro-dispersion water of titanium-group metal. Since the mechanism only involves plasma discharge in water between the electrode of titanium-group metal and its counter electrode, the apparatus can be constructed in a small size and therefore capital investment can be reduced. Consequently, micro-dispersion water of titanium-group metal can be obtained easily and economically.

Other characteristics of the present invention include the use of thus produced titanium-group metal micro-dispersion water, in which titanium-group metal is micro-dispersed, as a material for health products, cosmetics, food materials, drugs, quasi-drugs, etc., after necessary refining. The produced water contains a small amount of fine metal-oxide particles of larger particle size generated via bonding of titanium-group metal and oxygen and must therefore be filtered and refined as necessary.

So as not to remove the produced micro-dispersed titanium-group metal more than necessary, filtering should preferably be implemented not by using ion exchange or reverse-osmosis membrane, but by using the filter system as explained below that can yield micro-dispersion water suitable for a desired purpose. For example, filtering the processed water discharged from the water tank sequentially through hollow-fiber membranes is beneficial, because it will provide function water that can meet the required standards governing food and sanitation, cosmetics, drugs, etc.

The constituent analysis of the titanium-group metal micro-dispersion water obtained by the present invention found a trace amount of molten titanium-group metal in the high-pressure water.

An embodiment of the present invention is explained in details using an example in which titanium metal is used as the material. Note, however, that the material used in the present invention is not limited to titanium and that titanium-group metal micro-dispersion water can be obtained from other titanium-group metals through the same process.

EXAMPLE

FIG. 2 shows a representative example of the production apparatus proposed by the present invention.

The figure illustrates an apparatus for producing titanium micro-dispersion water by generating titanium ion vapor through plasma discharge in water and thereby causing the ion vapor to contact water and letting titanium micro-disperse in water, which comprising a water tank (3), a high-voltage discharge generator (1) equipped with a titanium metal electrode (6) and its counter electrode (7), a water inlet (8), an outlet for processed water (9), a discharge pump (10), an electrode-vibration/sliding device (5), and a titanium metal electrode feeder (4). A carbon electrode is used as the counter electrode. To produce 500 liters of titanium micro-dispersion water, titanium metal should be fed at a rate of 0.5 kg per hour for five hours, which achieves a titanium concentration of approx. 60 to 80 ppm.

Generated titanium micro-dispersion water is discharged from the water tank through the outlet, and supplied to a filter system if necessary, by means of the discharge pump. The filter system comprising hollow-fiber membranes of 50 microns, 25 microns, 3 microns, 0.5 micron and 0.1 micron, and by passing the produced water through these filter membranes sequentially a titanium micro-dispersion water containing a very small amount of molten titanium metal is obtained.

The titanium micro-dispersion water obtained in the above example contains super-fine titanium particles that will remain micro-dispersed in water in a stable manner for a long period of time without having to add any active agent.

A separate experiment was implemented under the same conditions, but in which zirconium metal was used as the material instead of titanium, also produced zirconium micro-dispersion water similar to the titanium micro-dispersion water obtained above.

Trial Test of High-Function Water:

Ten male and female subjects were instructed to apply or spray titanium micro-dispersion water in which titanium is micro-dispersed, and the health-promoting/bioactive effects and efficacies of the treatment were verified.

Use Conditions and Test Results 1. 10 male and female subjects (The subjects used the water at varying frequencies)

2. Efficacies

| | |
|---|---|
| Body feels lighter | 5 persons |
| Feels less fatigue | 8 persons |
| Fatigue disappears quicker | 7 persons |
| Condition of cold improved markedly | 1 person |
| Motor function improved | 6 persons |
| (Able to bend body further forward, jump further, etc.) | |
| Skin became smoother | 7 persons |
| Stiffness in shoulders decreased markedly | 7 persons |
| Eyes are no longer tired | 3 persons |
| Wounds heal quicker | 1 person |

As evident from the above test results, many of those who applied or sprayed the titanium micro-dispersion water obtained by the present invention cited decrease in fatigue, promotion of motor function, elimination of stiff shoulders, smoother skin and other improvements. Therefore, it is found that the titanium micro-dispersion water obtained by the present invention has remarkable effects as a material for health products, medical products and cosmetics.

INDUSTRIAL FIELD OF APPLICATION

The present invention provides newly developed titanium-group metal micro-dispersion water, as well as its production method and apparatus, and allows for efficient production of bioactive water containing titanium-group metal in micro-dispersed state. A number of trial tests also found that the obtained titanium-group metal micro-dispersion water is also useful as a material for health products, medical products, cosmetics, etc. Other tests also suggest remarkable effects of such water as healthy drinking water.

What is claimed:

1. A method for producing water in which super-fine metal particles of titanium-group metal are micro-dispersed, comprising the steps:
    (a) causing plasma discharge in water between a metal electrode made of titanium-group metal and its counter electrode to generate ion vapor of titanium-group metal constituting said metal electrode;
    (b) causing the generated metal ion vapor to contact, and micro-disperse in, water, thereby producing water in which super-fine particles of said metal of micron to nano-scale size are micro-dispersed; and
    (c) filtering the water produced from step (b) to remove fine particles of sizes larger than said micron to nano-scale size.

2. The method according to claim 1, wherein the counter electrode is made of carbon.

3. The method according to claim 1, further comprising vibrating or sliding the titanium-group metal electrode in water during the plasma discharge to prevent the electrode from fusing.

4. The method according to claim 1, further comprising adjusting a diameter and length of the counter electrode to change the amount of current flowing through the water.

5. A method for producing water in which super-fine metal particles of titanium, zirconium or hafnium are micro-dispersed, comprising the steps:
   (a) causing plasma discharge in water between a metal electrode made of titanium, zirconium or hafnium and its counter electrode to generate ion vapor of a metal constituting said metal electrode;
   (b) causing the generated metal ion vapor to contact, and micro-disperse in, water, thereby producing water in which super-fine particles of said metal of micron to nano-scale size are micro-dispersed; and
   (c) filtering the water produced from step (b) to remove fine particles of sizes larger than said micron to nano-scale size.

6. The method according to claim 5, wherein the counter electrode is made of carbon.

7. The method according to claim 5, further comprising vibrating or sliding the metal electrode made of titanium, zirconium or hafnium in water during the plasma discharge to prevent the electrode from fusing.

8. The method according to claim 5, further comprising adjusting a diameter and length of the counter electrode to change the amount of current flowing through the water.

* * * * *